United States Patent [19]

Dumitriu et al.

[11] Patent Number: 5,648,252
[45] Date of Patent: Jul. 15, 1997

[54] SUPPORTED POLYIONIC HYDROGELS CONTAINING BIOLOGICALLY ACTIVE MATERIAL

[75] Inventors: Severian Dumitriu, Sherbrooke, Canada; Itzhak Kahane, Har Adar; Hilda Guttmann, Jerusalem, both of Israel

[73] Assignees: Israel Fiber Institute State of Israel Ministry of Industry and Trade; Yissum Research Development Company of the University of Jerusalem, both of Jerusalem, Israel

[21] Appl. No.: 409,264

[22] Filed: Mar. 22, 1995

[30] Foreign Application Priority Data

Mar. 22, 1994 [IL] Israel ......... 109079

[51] Int. Cl.$^6$ ......... C12N 11/12; C12N 11/10; C12N 5/00; G01N 33/544
[52] U.S. Cl. ......... 435/179; 435/177; 435/178; 435/182; 435/397; 436/529; 436/530; 530/813; 530/814
[58] Field of Search ......... 435/174, 177, 435/178, 179, 182, 240.22, 240.23; 436/529, 530; 530/813, 814

[56] References Cited

U.S. PATENT DOCUMENTS

| | | | |
|---|---|---|---|
| 3,975,350 | 8/1976 | Hudgan et al. | 260/30.414 |
| 4,452,892 | 6/1984 | Roserear | 435/176 |
| 4,578,351 | 3/1986 | Roserear et al. | 435/41 |
| 4,744,933 | 5/1988 | Rha et al. | 264/4.3 |
| 5,116,747 | 5/1992 | Moo-Young et al. | 435/178 |

*Primary Examiner*—David M. Naff
*Attorney, Agent, or Firm*—Steinberg, Raskin & Davidson, P.C.

[57] ABSTRACT

A supported polyionic hydrogel containing biologically active material is prepared by impregnating into a porous support material a solution of anionic polysaccharide, a solution of cationic polysaccharide and a biologically active material. The anionic polysaccharide and the cationic polysaccharide react with each other to form a hydrogel containing the biologically active material. The hydrogel may be dried such as by lyophilization. The biologically active material can be in either polysaccharide solution or in another solution impregnated into the porous support material. A paper material or a textile material may be used as the porous support material. Preferably, the anionic polysaccharide is xanthan, dicarboxystarch or dicarboxycellulose and the cationic polysaccharide is chitosan. Especially preferred is a hydrogel formed from xanthan and chitosan. Biologically active materials in the hydrogel can be enzymes, antibody-producing cells or water-soluble drugs such as the antimicrobial agent, chlorohexidine.

10 Claims, No Drawings

SUPPORTED POLYIONIC HYDROGELS CONTAINING BIOLOGICALLY ACTIVE MATERIAL

BACKGROUND AND SUMMARY OF THE INVENTION

The present invention relates to polyionic hydrogels. More particularly, the present invention relates to biocompatible supported polyionic hydrogels which can be used in medicine and biotechnology, and which can serve as a carrier for pharmaceutically-active compounds, or for reactive immobilized enzymes or cultured cells producing antibodies.

Supported hydrogel, as well as hydrogels which act as carriers, are well-known in the art. Thus, e.g., acrylamide-$N,N^1$-methylenebisacrylamide was polymerized in a porous ceramic tube to form a permselective membrane composite useful for separating organic solvents from their water mixtures, as described in Chemical Abstracts, Vol. 113, No. 26, Abstract No. 233075v. In WO 8807075 there is described an enzyme reactor system composed of an enzyme entrapment hydrogel layer coated on a support and an ultraporous thin film membrane diffusion barrier.

In U.S. Pat. No. 4,668,654 there is described a hot or cold compress, comprising a layer of a substituted ureaurethane hydrogel material bonded to one side of a porous substrate, said hydrogel being formed from water, a polyol and a diisocyanate prepolymer. Similarly, in Japanese Patent 57119879, as abstracted in Chemical Abstracts, Vol. 98, No. 4, Abstract No. 1773j, there are described supported or self-supporting hydrogel polymer layers which were prepared using polymeric binders. For example, 2.0 kg ethylene-vinyl acetate copolymer in 8.0 kg PhMe was stirred with 2.0 kg powdered SGP polymer, to give a dispersion which was diluted with PhMe to a viscosity of 5 p and coated on a polyamide non-woven fabric.

In contradistinction, however, to said prior art supported hydrogels, the present invention provides a supported polyionic hydrogel formed by the interaction between an anionic polysaccharide and a cationic polysaccharide while in contact with a cellulose or synthetic fibre or a mixture thereof, or with a natural or synthetic polymer of a combination thereof, to form a fiber, fabric, sheet, or other stable woven, non-woven, or knitted material having said polyionic hydrogel incorporated therein.

In U.S. Pat. No. 4,452,892 to Rosevear, there is disclosed the application of a gel precursor which contains a biologically active material onto a support material, followed by a polymerization of the gel precursor to form a supported, biologically active, material-containing hydrogel. Similarly, U.S. Pat. No. 4,578,351 to Rosevear, et al., discloses the production of chemical compounds with immobilized plant cells.

In U.S. Pat. No. 4,744,933 to Rha, et al., there is disclosed the encapsulation of an active material within a membrane formed by the reaction of an anionic polymer such as xanthan with a cationic polymer such as chitosan.

U.S. Pat. No. 5,116,747 to Moo-Young, et al., discloses the immobilization of a biologically active material within the pores of a fibrous chitosan-alginate matrix.

None of said patents, however, teaches or suggests the supported hydrogels of the present invention as defined and exemplified herein.

In preferred embodiments of the present invention, said anionic polysaccharide is selected from xanthan, dicarboxystarch and dicarboxycellulose, and said cationic polysaccharide is chitosan.

Especially preferred is a supported polyionic hydrogel formed by the interaction between xanthan and chitosan.

As will be realized, the prior art hydrogels were first formed and then coated onto a supporting fabric or film, while in the present invention the hydrogel is itself formed while in contact with a cellulose or synthetic fibre or a mixture thereof, or while in contact with a natural or synthetic polymer or a combination thereof, to form a fiber, fabric, sheet, or other stable woven, non-woven, or knitted material having said polyionic hydrogel incorporated therein.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

DETAILED DESCRIPTION OF THE INVENTION

EXAMPLE 1

Impregnation of Woven Cotton Fabric with Hydrogel and Antimicrobial Agents

Pieces of woven cotton fabric were impregnated with hydrogel and antimicrobial agents by immersing them in 10 ml of various solutions (0.1% xanthan, 0.3% chitosan, 0.2% of chlorohexidine gluconate, or 1% iodine ($I_2$+KI). The schedule of sequence of impregnation is outlined in Table 1. The incubation in the xanthan solution was for 5 min, except for 10 min. for samples 7 and 8. In the chitosan solution, it was 10 min. with no exceptions. The length of incubation in the chlorohexidine solution was 3 or 5 min., and in the $I_2$+KI solution 5 or 10 min.; all are indicated in Table 1. At the end of an incubation period, the excess solution was removed by squeezing of the fabric, and the sample was weighed and transferred to the next incubation step. The WPU and DPN of the various samples is outlined in Table 1.

The antimicrobial activities of the various samples were assessed as follows: The antimicrobial activity of the product was tested on lawns of several bacteria: Staphylococcun aureus (SA); S.epidermidis (SE); Escherichia coli (EC); and Pseudonomas aeruginosa (PA), inoculated on agar plates by placing a sample of about 2 $cm^2$ on the surface of the plate and measurements of the inhibition zone after growth of the bacteria for 18 hours at 37° C. The results are summarized in Table 2.

The data in Table 1 and hereinafter are presented as follows: (a) no inhibition; (x–y) growth inhibition in mm.; x=minimum distance, y=maximum distance.

TABLE 1

Impregnation of woven cotton fabric with hydrogels and drugs.

| Sample | Treatment Schedule | | | Xanthan | Chitosan | Chlorohexidine | | Xanthan + I₂ | | I₂ | | |
|---|---|---|---|---|---|---|---|---|---|---|---|---|
| # | 1 | 2 | 3 | WPU % | WPU % | min. | WPU % | min. | WPU % | min. | WPU % | DPU % |
| 1 | XA | CHI | — | 119.6 | 123.5 | — | — | — | — | — | — | 9.5 9.1 |
| 2 | CHI | I₂ | — | — | 129.7 | — | — | — | — | x/10 | 146.6 | 29.17 28.07 |
| 3 | CHX | XA | CHI | 124.9 | 118.9 | x/3 | 133.8 | — | — | — | — | 10.5 9.8 |
| 4 | XA | CHX | CHI | 123.22 | 126.2 | x/5 | 130.2 | — | — | — | — | 11.6 |
| 5 | XA | I₂ | CHI | 126.0 | 121.2 | — | — | — | — | x/5 | 146.7 | 14.7 |
| 6 | XA | I₂ | CHI | — | 123.9 | — | — | x/10 | 119.2 | — | — | 11.5 10.8 |
| 7* | XA | CHX | — | 137.4 | — | x/5 | 149.7 | — | — | — | 11.9 | — |
| 8* | CHX | XA | — | 166.6 | — | x/5 | 164.4 | — | — | — | 3.5 16.8 | — |

* = drip drying
WPU = wet pickup, DPU = dry pickup
xanthan = XA; chitosan = CHI; chlorohexidine = CHX; I₂ + KI = I₂

It is indicated in Table 2 that antimicrobial agents can be included in the hydrogel, and that the sequence of impregnation was important.

TABLE 2

Antimicrobial activity of woven cotton fabric impregnated with hydrogels and antimicrobial agents

| Sample* | SA | EC | PA | SE |
|---|---|---|---|---|
| 1 | a | a | a | a |
| 2 | 4–5 | 3–5 | 2–3 | 5–8 |
| 3 | 3–4 | 2–4 | 0–1 | 3–4 |
| 4 | 3–4 | 3–4 | 1–2 | 3–4 |
| 5 | 0–1 | 0–4 | a | 0–1 |
| 6 | 24 | 2–3 | 1–2 | 2–3 |
| 7 | 3–5 | 3–5 | 2–4 | 4–7 |
| 8 | 3–4 | 3–4 | 2–3 | 4–5 |

*The sample impregnation is described in Table 1.

EXAMPLE 2

The Inclusion of the Hydrogel Urease System into Paper and Woven Cotton Fabric

In the first step, a piece of filter paper and a piece of woven cotton fabric were immersed for 10 min in a solution containing a mixture of xanthan and urease (10 ml 0.3% xanthan+100 μl urease). The excess xanthan-urease solution was removed by squeezing. The wet pick-up for the paper and cotton was about 126% and 132%, respectively. The samples were immersed for 10 min. in a solution of 0.3% chitosan, pH 6.4. The samples were then squeezed again. The wet pick-up was about 128% for both samples. The samples were dried at room temperature.

The urease activity in the hydrogel urease system was determined by measuring the release of ammonia from the urea, as detected by a modified Berthelots reaction. This was conducted as follows: Weighed samples of paper and cotton impregnated with the hydrogel-urease system, as described above, were immersed for 15 min. in a vessel containing 500 μl of 50 mM urea in HED buffer [50 mM N-2-hydroxyethylpiperazine tetraacetic acid, 3 mM ethylenediamine-tetraacetic acid, 1 mM dithiothreitol (Sigma Chemicals, Israel)], pH 7.0, and then 1 ml of 25 mMNaOH was added to the reactor. Samples of 100 μl were withdrawn in order to measure the amount of ammonia released from urea, using the Berthelots reaction. Absorbance of the reaction mixtures was measured spectrophotometrically at 625 nm.

Most of the enzyme was included in the hydrogel, as only about 5% of its activity was detected in the xanthan urease solution at the end of the first step. The enzymic activity was measured in the hydrogel on support after storage for one day or two weeks, with only about 30% loss (Table 2).

As seen in Table 3, about 70% of the urease activity was detected even after two weeks' storage on the hydrogel, on both paper and cotton supports. Comparable results were found for the urease activity on the xanthan-chitosan hydrogel without the support, as described below in Example 3.

EXAMPLE 3

Immobilization of Urease in Hydrogel

Urease (300 μl) in HED buffer was added to 30 ml of 0.3% xanthan and stirred. Then 30 ml of the 0.3% chitosan solution, at pH 6.4, were added. The gel formed was stirred for 15 min. at room temperature. The mixture was centrifuged for 15 min. at 15,000 rpm. The supernatant was removed and the gel washed with 2 ml of the HED buffer. The gel was separated by centrifugation and was lyophilized and stored at −20° C. The urease activity in the hydrogel was assayed as described above in Example 2, and the results are summarized in Table 3. The urease also retained its activity in this hydrogel after lyophilization and rehydration.

TABLE 3

Activity of hydrogel urease system

| Sample | Urease activity (%) |
|---|---|
| Hydrogel on paper (after 1 day) | 100 |
| Hydrogel on paper (after 2 weeks) | 68 |
| Hydrogel on cotton (after 1 day) | 100 |
| Hydrogel on cotton (after 2 weeks) | 70 |
| Hydrogel (by itself) after 1 day | 100 |
| | 84 |

TABLE 3-continued

Activity of hydrogel urease system

| Sample | Urease activity (%) |
|---|---|
| after 2 weeks | 68 |
| Hydrogel lyophylized | 1.472 |

EXAMPLE 4

Inclusion of Cells in Hydrogels

A suspension of monoclonal antibody-producing cells, containing $10^5$/ml cells, was centrifuged for 5 min at 15,000 rpm. The cells were suspended in 10% FCS+DMEM. A solution of 0.3% xanthan and a solution of 0.3% chitosan at pH 4.2 were separately sterilized for 1.5 h. The solution of chitosan was neutralized under sterile conditions with sterile (filtered) 1.5% $NaHCO_3$ until the pH reached the value of 6.2–6.4 (by pH paper). 18 ml of the cell suspension in DMEM were added to the 20 ml solution of 0.3% xanthan. Then 20 ml of a solution of 0.3% chitosan was added and stirred. The gel formed was separated when the supernatant was aspirated, and 50 ml fresh DMEM at 37° C. was added. The cells were incubated in 5% $CO_2$+air at 37° C. Samples were drawn after 24 h. and 72 h., and tested for MAb production.

TABLE 4

Monoclonal antibody production by cells in hydrogel

| | CPM |
|---|---|
| Medium | 300 |
| Cells 24 h | 610 |
| Cells 72 h | 920 |

MAb was assessed by radioimmunoassay

As seen in Table 4, the cells continued to produce the monoclonal antibodies for at least 4 days after inclusion in the hydrogel.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A supported polyionic hydrogel containing a biologically active material formed by a method comprising the steps:

a) impregnating into a porous support material a solution of an anionic polysaccharide selected from the group consisting of xanthan, dicarboxystarch and dicarboxycellulose, and b) impregnating into the porous support material from a) a chitosan solution, whereby said anionic polysaccharide and said chitosan react with each other while in contact with and impregnated into said porous support to produce a polyionic hydrogel impregnated into said porous support material, said biologically active material being in said anionic polysaccharide solution or said chitosan solution or in a separate solution impregnated into said porous support material.

2. The supported polyionic hydrogel according to claim 1, wherein said anionic polysaccharide is xanthan.

3. The supported polyionic hydrogel according to claim 1, wherein the biologically active material is a pharmaceutically active compound.

4. The supported polyionic hydrogel according to claim 3, wherein said compound is a water-soluble drug.

5. The supported polyionic hydrogel according to claim 4, wherein said water-soluble drug is an antimicrobial agent.

6. The supported polyionic hydrogel according to claim 5, wherein said antimicrobial agent is chlorohexidine.

7. The supported polyionic hydrogel according to claim 1, wherein said biologically active material is an enzyme.

8. The supported polyionic hydrogel according to claim 1, wherein said biologically active material is antibody producing cells.

9. The supported polyionic hydrogel according to claim 1, wherein said polyionic hydrogel impregnated in said porous support material is dehydrated.

10. The supported polyionic hydrogel according to claim 1, wherein said porous support material is selected from the group consisting of a paper material and a textile material.

* * * * *